(12) United States Patent
Duhaut et al.

(10) Patent No.: US 9,095,663 B2
(45) Date of Patent: Aug. 4, 2015

(54) BIOLOGICAL FLUID FILTRATION UNIT PROVIDED WITH AN OFFSET INLET AND/OR OUTLET MEMBER

(75) Inventors: Robert Duhaut, Comines (FR); Chryslain Sumian, Lambersart (FR); David Godard, Tourcoing (FR)

(73) Assignee: MACO PHARMA, Mouvaux (FR)

( * ) Notice: Subject to any disclaimer, the term of this patent is extended or adjusted under 35 U.S.C. 154(b) by 1012 days.

(21) Appl. No.: 12/597,276

(22) PCT Filed: Apr. 22, 2008

(86) PCT No.: PCT/FR2008/000570
§ 371 (c)(1),
(2), (4) Date: Oct. 23, 2009

(87) PCT Pub. No.: WO2008/145847
PCT Pub. Date: Dec. 4, 2008

(65) Prior Publication Data
US 2010/0108596 A1    May 6, 2010

(30) Foreign Application Priority Data
Apr. 25, 2007  (FR) ...................................... 07 03012

(51) Int. Cl.
*A61M 1/36*  (2006.01)
*A61M 1/02*  (2006.01)
(Continued)

(52) U.S. Cl.
CPC ........... *A61M 1/3633* (2013.01); *A61M 1/0209* (2013.01); *A61M 1/0218* (2014.02); *A61M 1/3636* (2014.02); *A61M 1/3686* (2014.02);
(Continued)

(58) Field of Classification Search
CPC ..................... A61M 1/209; B29C 66/53262
USPC .................................................. 210/252, 489
See application file for complete search history.

(56) References Cited

U.S. PATENT DOCUMENTS

| 4,732,299 A * | 3/1988 | Hoyt ............................... 222/94 |
| 6,367,634 B1 * | 4/2002 | Lynn et al. .................... 210/489 |
| 6,688,476 B2 * | 2/2004 | Breillatt et al. ............... 210/435 |

FOREIGN PATENT DOCUMENTS

| FR | 2677883 A1 * | 12/1992 | ................ A61J 1/00 |
| FR | 2821762 A1 | 9/2002 | |

(Continued)

OTHER PUBLICATIONS

International Search Report dated May 13, 2009.

*Primary Examiner* — Tony G Soohoo
*Assistant Examiner* — Peter Keyworth
(74) *Attorney, Agent, or Firm* — Bachman & LaPointe, P.C.

(57) ABSTRACT

A filtration unit intended to allow the selective elimination of target substances from a fluid such as flood or a blood component, has an outer envelope formed from two flexible sheets joined together over their periphery along a bond line so as to define an inner volume, the envelope containing a filtering medium which delimits, on both sides of the bond line, an inlet compartment of the fluid to be filtered and an outlet compartment of the filtrate, each of the compartments being provided with an element—respectively an inlet and outlet element—for bringing the compartment into communication with the outside, the elements being connected between the sheets and comprising a flow channel that passes through the bond line, the unit being characterized in that at least one channel is offset relative to the bond line towards the compartment with which the channel is in communication.

15 Claims, 6 Drawing Sheets (51) Int. Cl.
  *B29C 65/02* (2006.01)
  *B29C 65/04* (2006.01)
  *B29C 65/00* (2006.01)
  B29L 31/14 (2006.01)
  B29L 31/00 (2006.01)

(52) U.S. Cl.
  CPC ............... *B29C 65/02* (2013.01); *B29C 65/04* (2013.01); *B29C 66/53262* (2013.01); *B29C 66/53263* (2013.01); *B29C 66/80* (2013.01); *B29C 66/81431* (2013.01); *B29C 66/83221* (2013.01); *B29C 66/8432* (2013.01); *B29C 66/81423* (2013.01); *B29L 2031/14* (2013.01); *B29L 2031/7148* (2013.01)

(56) References Cited

FOREIGN PATENT DOCUMENTS

| | | |
|---|---|---|
| JP | 7067952 A | 3/1995 |
| WO | 0156679 A1 | 8/2001 |

* cited by examiner

BIOLOGICAL FLUID FILTRATION UNIT PROVIDED WITH AN OFFSET INLET AND/OR OUTLET MEMBER

BACKGROUND (1) Field of the Invention

The invention relates to a filtration unit for the selective removal of target substances from a fluid such as blood or a blood component, and a method for manufacturing such a unit and a bag system comprising same.

It typically applies to the filtration of blood or a blood component to remove undesirable substances for transfusion, such as leukocytes, pathogens, prion proteins and/or substances used in pathogen inactivation and/or removal methods.

The blood or blood component, after the collection and separation thereof in the case of a component, is particularly intended to be transfused to a patient needing same. During transfusion, it is well known that leukocytes are undesirable in that they are liable to induce adverse and/or potentially dangerous reactions in the patient.

The same applies for certain substances such as the prion, the agent responsible for cases of transmissible subacute spongiform encephalopathy, particularly the Creutzfeld-Jacob disease variant in humans since recent studies have demonstrated a likely risk of prion transmission in blood transfusions.

To remove said undesirable substances, filtration units comprising a flexible outer casing containing a porous medium and provided with at least one inlet orifice and at least one outlet orifice wherebetween the fluid to be filtered flows in one direction are already known. The porous medium defines with the outer casing an inlet compartment for the fluid to be filtered and an outlet compartment for the filtrate.

In such units, illustrated for example by the document EP-A-526 678, the nozzles providing the inlet and outlet orifices are arranged symmetrically between two sheets forming the outer casing.

The document JP-3132307 describes a method used to seal a nozzle between two flexible sheets. According to this method, a stack consisting successively of a first flexible sheet, the nozzle and a second flexible sheet, is arranged between two identical moulds. A metal tube is inserted into the nozzle and a high-frequency dielectric current is sent into the mould to seal the nozzle with the sheets. As the two moulds holding the nozzle between the sheets are symmetrical, the seal is thus aligned on a diameter of the nozzle.

With such a method applied to the manufacture of filtration units, as described in the document WO-A1-01 56679, the flow of the fluid at the inlet and at the outlet of the filtration unit is not optimal. Indeed, due to the thickness thereof, the porous medium faces the opening of the inlet and outlet nozzle, impeding the circulation of the fluid in the filtration unit. In particular, the filling of the inlet compartment and draining of the outlet compartment are slowed down.

So that the inlet and/or outlet orifice opens directly into the inlet and/or outlet compartment without being impeded by the thickness of the porous medium, sealing a moulded part serving as a fluid inlet and/or outlet orifice on the surface of each of the flexible sheets has been envisaged. Such units are for example described in the document WO-A1-01 91880.

However, with such moulded parts, the wetting of the filtration medium is not optimised as the blood arrives perpendicular to the filtration medium. Furthermore, the sealing of said moulded parts on the surface of the sheets complicates the method for manufacturing filtration units and increases the cost thereof.

SUMMARY OF THE INVENTION

The invention is intended to improve the flow of the fluid in a flexible filtration unit, simply, by providing a filtration unit wherein the fluid flows readily in the inlet and/or outlet compartments of the filtration unit and wherein the wetting of the filtering agent is homogeneous.

To this end, according to a first aspect, the invention relates to a filtration unit for the selective removal of target substances from a fluid such as blood or a blood component, comprising an outer casing formed from two flexible sheets joined together on the periphery thereof along a joint face so as to define an inner volume, the casing containing a filtering medium which defines, on either side of said joint plane, an inlet compartment of the fluid to be filtered and a filtrate outlet compartment, each of the compartments being provided with a member, an inlet and outlet member respectively, for connecting said compartment with the outside, said members being joined between the sheets and comprising a flow conduit through the joint face, at least one conduit being offset with respect to the joint face towards the compartment wherewith said conduit is connected.

According to a second aspect, the invention relates to a method for manufacturing a filtration unit according to the first aspect wherein one of the inlet or outlet members is formed from a nozzle, said method providing steps consisting of:

providing two moulds mutually forming the joint face, said moulds each being provided with at least one form, said forms mutually forming a housing for receiving the nozzle and being dissymmetrical so as to position said nozzle offset with respect to the joint face;

arranging between the moulds a stack formed from the filtering medium between the flexible sheets, a nozzle being arranged in the joint face and facing the forms;

joining the filtration unit by closing the moulds.

According to a third aspect of the invention, the invention relates to a bag system for removing target substances from a biological fluid such as blood or a blood component, comprising:

a filtration unit according to the first aspect of the invention; and a filtrate collection bag, said bag being connected, via a nozzle and at an inlet orifice, to the filtration unit outlet conduit.

BRIEF DESCRIPTION OF THE DRAWINGS

Other aims and advantages will emerge in the course of the description hereinafter with reference to the appended figures.

DETAILED DESCRIPTION OF THE PREFERRED EMBODIMENT(S)

The invention relates to a filtration unit for the selective removal of target substances from a fluid such as blood or a blood component.

The filtration is particularly used for filtering whole blood from a blood donation or a blood component such as a red blood cell concentrate, a plasma, a platelet-rich plasma or a platelet concentrate, obtained by separating whole blood.

Figure 1:
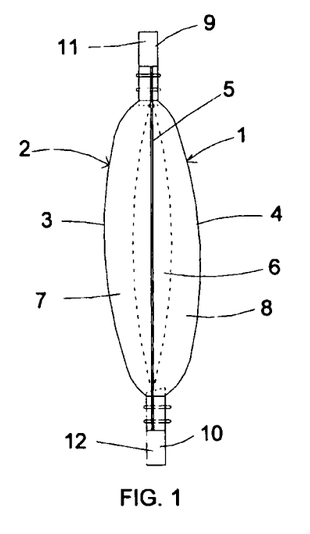
FIG. 1 represents schematically a profile view of the filtration unit according to a first embodiment of the invention wherein the inlet and outlet members are formed from a nozzle.
Figure 2:
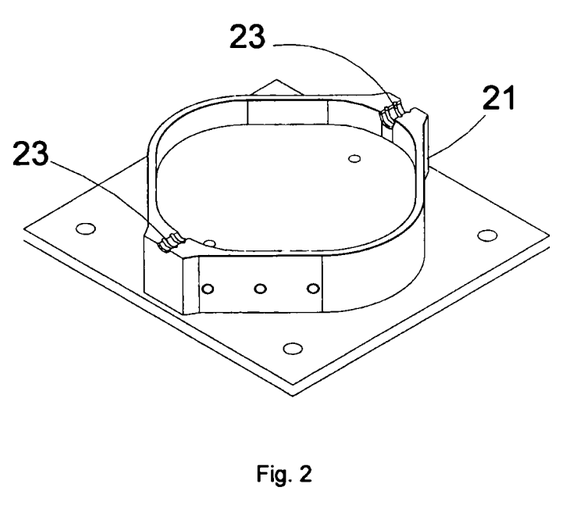
FIG. 2 represents schematically a mould used in the manufacture of a filtration unit according to FIG. 1.
Figure 3:
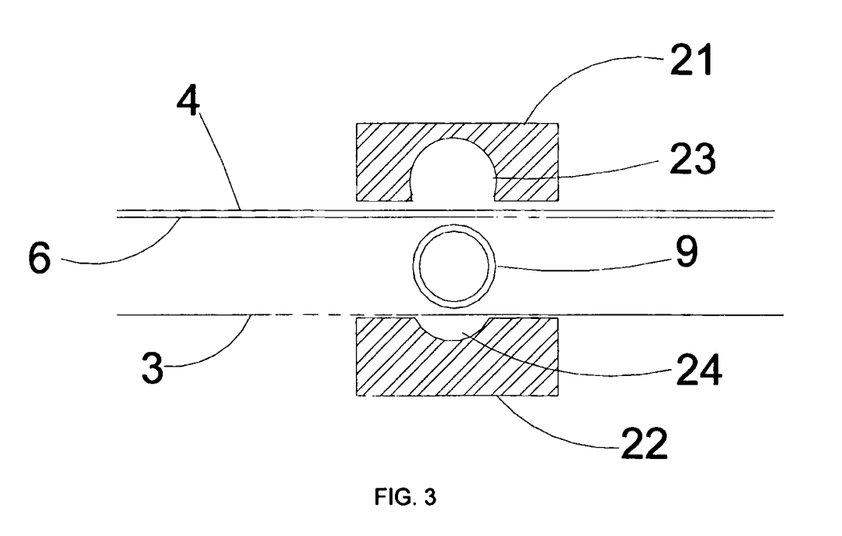
FIGS. 3 to 5 represent schematically the steps of the method for manufacturing a filtration unit represented in FIG. 1.
Figure 4:
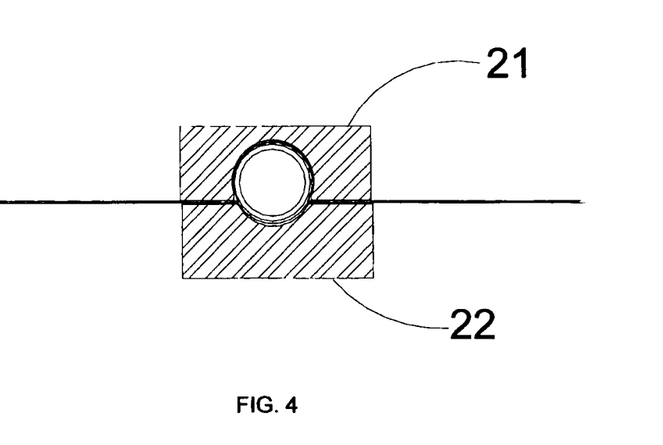

According to FIG. 1, the filtration unit 1 is flexible, i.e. it comprises an outer casing 2 formed from two flexible sheets 3, 4 joined together on the periphery thereof along a joint face 5 so as to define an inner volume.

The flexible sheets 3, 4 are made of a flexible thermoplastic material suitable for sterilisation, such as polyvinyl chloride. They are joined together by bonding or sealing, particularly by means of high-frequency sealing.

The casing 2 of the filtration unit contains a filtering medium 6 which defines, on either side of said joint face, an inlet compartment 7 of the fluid to be filtered and a filtrate outlet compartment 8.

According to the filtering medium contained in the filtration unit, the filtration unit is used to remove or reduce the quantity of target substances such as leukocytes, pathogens including viruses and bacteria, prion proteins and/or substances used in methods for removing pathogens from blood. Such substances are for example photosensitive compounds such as methylene blue or psoralen.

Each of the compartments is provided with an inlet or outlet member 9, 10 respectively for connecting said compartment 7, 8 with the outside, said members 9, 10 being joined between the sheets 3, 4 and comprising a flow conduit 11, 12 through the joint face 5.

The positioning of the members 9 and 10 between the flexible sheets 3 and 4 provides a plurality of advantages. Firstly, in terms of production, the insertion of the members between two flexible sheets and the joining thereof can be readily automated.

Further, in terms of filtration, the fluid flows naturally from the top of the unit to the bottom of the unit, enabling the use of the entire surface of the filtering medium and the reduction of the volume of blood present in the filter after filtration.

Finally, during the centrifugation of a bag system comprising such a filtration unit, the flat surfaces of the filtration unit are not liable to damage the other components of the bag system.

According to the invention, at least one conduit 11, 12 is offset with respect to the joint face 5 on the side of the compartment 7, 8 wherewith said conduit is connected.

Unlike the filtration units of the prior art wherein the inlet and outlet conduits arranged between the sheets forming the casing are centred with respect to the joint face, at least one of the conduits 11, 12 of the filtration unit according to the invention is off-centre with respect to the joint face 5.

In this way, the conduit 11, 12 opens into the compartment 7, 8 at a more removed point from the filtering medium 6 than when the conduit is arranged symmetrically with respect to the joint face 5.

Therefore, even when the filtering medium 6 has a significant thickness, the conduit 11, 12 is not blocked or impeded by the filtering medium 6 and the flow of the fluid is enhanced. Blocking phenomena of the filtration unit 1 are limited.

Furthermore, the offset position of the conduit 11, 12 creates, in conjunction with the flexible sheets 3, 4 forming the outer casing 2, an additional gap between the filtering medium 6 and the outer casing 2 which increases the volume of the compartment 7, 8 particularly where the conduit 11, 12 opens into said compartment 7, 8. This additional volume facilitates the flow of the fluid through the filtration unit 1.

Advantageously, the filtration unit 1 comprises an inlet conduit 11 and an outlet conduit 12, said conduits being offset on either side of the joint face 5.

When the inlet conduit 11 is offset, the fluid flowing from the conduit is distributed on the entire surface of the filtering medium 6, facilitating the activation of the filtration unit.

When the outlet conduit 12 is offset, the dead volume of the filtration unit is reduced as the fluid flows more readily from the outlet compartment 8.

According to a specific embodiment of the filtration unit 1, the flow in the conduit 11, 12 extends along a direction substantially parallel with the joint face 5.

In this way, in the inlet compartment 7, direct contact of the fluid with the filtering medium 6 is avoided, reducing the risk of red blood cell haemolysis if the fluid is blood.

This flow parallel with the joint face also ensures improved distribution of the flow on the entire surface of the filtering medium 6 and prevents the blockage of the filtration unit 1.

According to a first embodiment represented in FIG. 1, at least one member 9, 10 for connecting a compartment 7, 8 with the outside is formed from a flow nozzle, said nozzle having an outer radius R and the offset distance of said nozzle with respect to the joint face being strictly less than R.

Figure 5:
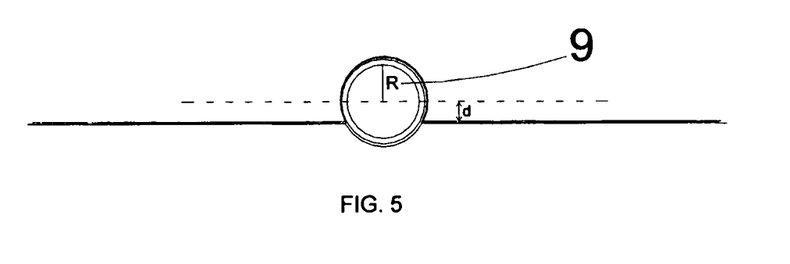

The offset distance d (FIG. 5) is the interval between the centre of the nozzle in the symmetrical position thereof with respect to the joint face 5 and the centre of the nozzle in the offset position thereof.

In particular, the offset distance is between 20% and 80% of the radius R. This offset distance reduces the risks of leaks on the nozzle liable to occur during the sealing of the nozzle with the flexible sheets 3, 4.

In particular, the offset distance is 33% of the radius R. This distance is large enough to obtain the advantages provided by the offset of the connection member, particularly the lack of obstruction of the conduit by the filtering medium, and small enough to ensure the tightness of the join between the flexible sheets 3, 4 and the nozzle.

According to another embodiment represented in FIGS. 6 to 11, the filtration unit is provided with at least one member 9, 10 comprising a body topped with a flow conduit 11, 12, said body being arranged substantially symmetrically with respect to the joint face 5.

Figure 6:
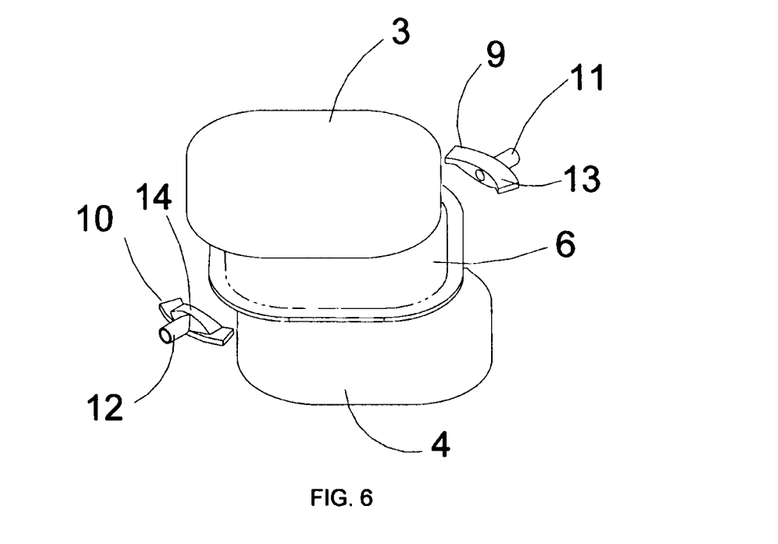
FIG. 6 represents schematically the various components of a filtration unit according to a second embodiment of the invention wherein the inlet and outlet members are formed from a rigid member.

A first example of a body is illustrated in FIG. 6. The body comprises a first flat portion 13 and a second rounded portion 14 wherethrough a conduit 11, 12 passes.

Figure 7:
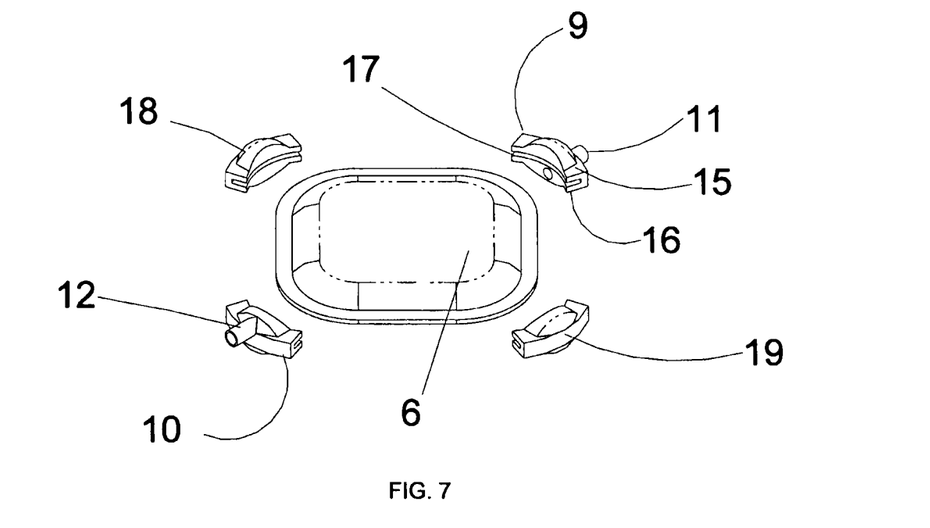
FIG. 7 represents schematically an alternative embodiment of the filtration unit according to the second embodiment, the outer casing not being shown.
Figure 8:
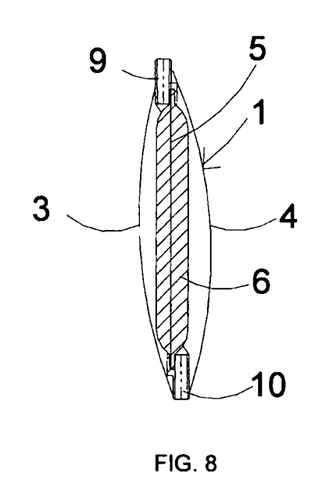
FIG. 8 represents schematically a sectional view of the filtration unit represented in FIG. 7.
Figure 9:
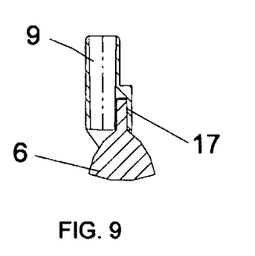
FIG. 9 represents schematically an enlarged view of one of the inlet or outlet members of the filtration unit according to FIG. 7.

According to FIGS. 7 to 9, the body comprises a first part 15 and a second part 16, each part having a rounded portion extended on either side by a flat portion. This shape facilitates the joining of the flexible sheet 3, 4 and the member 9, 10.

The body further comprises a slot 17 between the first part 15 and the second part 16 wherein the filtration medium 6 is inserted. Advantageously, the first and second parts 15, 16 are symmetrical with respect to said slot 17.

The second part 16 of the body comprises a conduit 11, 12 passing through same and opening above the slot 17. Said conduit is intended to be connected to a nozzle of a bag system.

This member is particularly made of a rigid plastic suitable for sterilisation such as a polyolefin, particularly polypropylene.

In particular, the member is formed by moulding such a rigid material.

As shown in FIG. 9, this member makes it possible to obtain greater conduit offset distances in the filtration unit than with a nozzle.

According to FIG. 7, the filtering medium is held between two moulded members 9, 10 as described above, diametrically opposite each other.

To simplify the manufacture of the filtration unit, two support members 18, 19, similar to the inlet and outlet members 9, 10 devoid of a conduit are provided. These support members are diametrically opposed.

Furthermore, these support members 18, 19 in conjunction with the inlet and outlet members 9, 10 make it possible to maintain a gap between the flexible sheets 3, 4 forming the casing of the filtration unit and the filtering medium, thus facilitating the flow.

Figure 10:
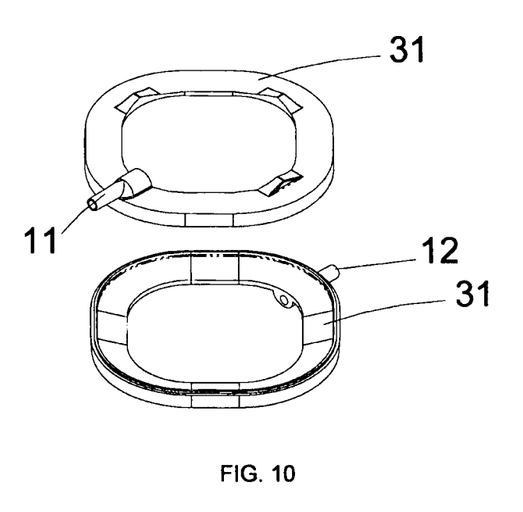
FIGS. 10 and 11 represent schematically another alternative embodiment of the inlet and outlet members of a filtration unit according to the second embodiment.
Figure 11:
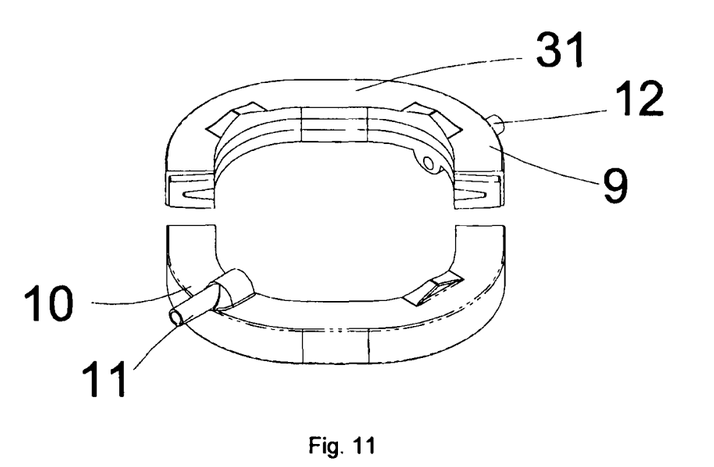

According to the alternative embodiments shown in FIGS. 10 and 11, the filtering medium is held in a rigid frame 31, the frame between topped by two flow conduits 11, arranged on either side of the filtering medium 6. The frame is for example formed from two separate parts.

Advantageously, the filtering medium 6 is held in the filtration unit 1 substantially symmetrically with respect to the joint face 5, such that the volume of the inlet compartment is substantially equal to the volume of the outlet compartment.

Figure 12:
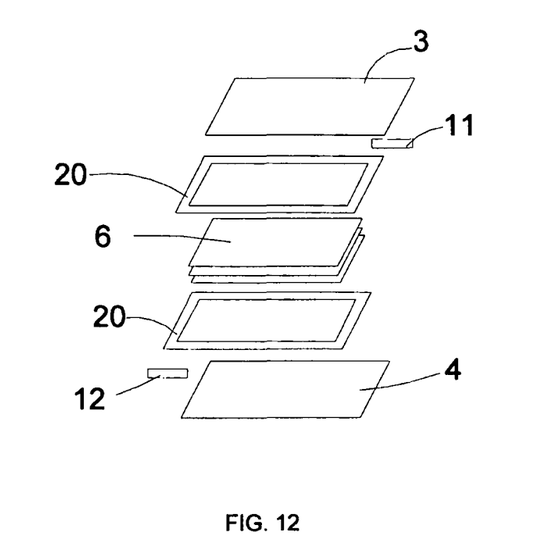
FIG. 12 represents schematically the various components of a filtration unit according to FIG. 1 according to a first alternative embodiment.

For this purpose, according to a particular embodiment represented for example in FIG. 12, the filtration unit 1 comprises a tight flexible frame 20 wherein the filtering medium 6 is positioned, said frame 20 being rigidly connected between the sheets 3, 4 along the joint face.

In particular, the flexible frame is made of flexible thermoplastic material suitable for sterilisation, such as polyvinyl chloride.

A more detailed description of the flexible frame is found in the document EP-A-526 678.

The offset of the inlet and outlet members 9, 10 enables the reduction of the width of the flexible frame 20 and therefore the limitation of the dead volume of the filtration unit 1.

Figure 13:
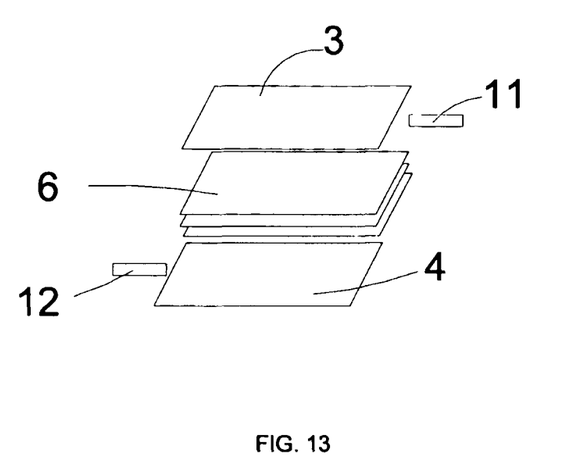
FIG. 13 represents schematically the various components of a filtration unit according to FIG. 1 according to a second alternative embodiment.

In an alternative embodiment represented in FIG. 13, the filtering medium 6 is rigidly connected between the sheets 3, 4 along the joint face or at a distance from the periphery of the sheets.

The rigid connection of the filtering medium in the filtration unit is produced by means of bonding or sealing, particularly by means of high-frequency sealing.

In a flexible filtration unit, during filtration, the sheet 4 forming the outlet compartment 8 tends to adhere to the filtering medium 6 and block the fluid flow.

To prevent this drawback, the outlet compartment is disengaged from the filtering medium by the presence of one or a plurality of separating rings, arranged between the filtering medium and the flexible outer casing, inside the outlet compartment.

The offset of the outlet member in the filtration unit also helps disengage the filtering medium from the flexible outer casing.

In an alternative or combined embodiment, to increase the gap between the flexible outer casing and the filtering medium, a part of the filtration unit conduit extends inside the compartment wherewith said conduit is connected (not shown).

According to a second aspect of the invention, a method for manufacturing a filtration unit 1 comprising an inlet and/or outlet member 9, 10 in the form of a nozzle will now be described in relation with FIGS. 2 to 5.

The method envisages steps consisting of:
  providing two moulds 21, 22 mutually forming the joint face 5, said moulds each being provided with at least one form 23, 24, said forms mutually forming a housing for receiving the nozzle and being dissymmetrical so as to position said nozzle offset with respect to the joint face;
  arranging between the moulds a stack formed from the filtering medium 6 between the flexible sheets 3, 4, a nozzle being arranged in the joint face and facing the forms 23, 24;
  joining the filtration unit 1 by closing the moulds 21, 22.

In particular, the join is produced by sealing, particularly high-frequency sealing. When the moulds are compressing the stack, high-frequency energy is applied thereto so as to produce the seal.

In the stack, the filtering medium 6 is either positioned directly between the flexible sheets 3, 4 forming the casing 2, or held in a flexible frame 20 as described above.

In the latter cases, the seal on the offset nozzle comprises the flexible sheets 3, 4 forming the outer casing and the flexible frame 20.

Figure 14:
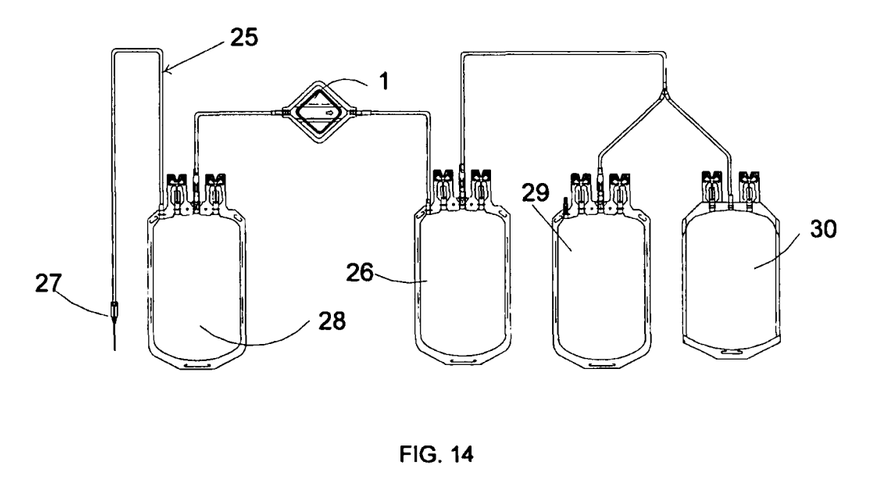
FIG. 14 represents schematically a bag system comprising a filtration unit according to the invention.

According to a third aspect of the invention, a bag system for removing target substances from a biological fluid such as blood or a blood component is described, comprising:
  a filtration unit 1 according to the first aspect of the invention; and
  a filtrate collection bag 26, said bag being connected, via a nozzle and at an inlet orifice, to the filtration unit 1 outlet conduit 10.

FIG. 14 represents an example of a bag system used to filter whole blood from a donation and to separate same into plasma and red blood cell concentrate.

The system comprises a needle 27 to draw a donor's blood, a whole blood collection bag 28, a filtration unit 1 as described above for filtering leukocytes from blood, a filtrate collection bag 26, and two satellite bags 29, 30 for collecting plasma and red blood cells after centrifuging the filtrate collection bag. The bags 26, 28, 29, 30 and the filtration unit 1 are connected by means of flexible nozzles suitable for sterilisation.

The system is advantageously closed, i.e. the various members are pre-connected to each other at the time of manufacture. Once the whole blood has been collected in the collection bag, the filtration and separation steps are performed without contact with the ambient air.

With such a bag system according to the invention, improved blood flow through the filtration unit has been observed.

The invention claimed is:

1. A filtration unit for the selective removal of target substances from a fluid comprising an outer casing formed from two flexible sheets joined together on the periphery thereof along a joint face so as to define an inner volume, the outer casing containing a filtering medium which defines, on either side of said joint face, an inlet compartment of the fluid to be filtered and a filtrate outlet compartment, each of the compartments being provided with an inlet and outlet member respectively, for connecting said compartment with the outside, said members being joined between the sheets and said inlet member comprising a first flow conduit through the joint face, said outlet member comprising a second flow conduit through the joint face, and at least one of said first and second conduits being offset with respect to the joint face towards the compartment wherewith said at least one of said first and second conduits is connected, wherein at least one of the members for connecting a compartment with the outside is formed from a flow nozzle, said flow nozzle having an outer radius R, wherein, from a profile view of the filtration unit, the joint face is offset by an offset distance d with respect to a symmetry plane of said flow nozzle, wherein said symmetry plane is parallel to said joint face and passes through a center of said flow nozzle, wherein said offset distance is between 20% and 80% of the radius R.

2. The filtration unit according to claim 1, wherein said conduits are offset on either side of the joint face.

3. The filtration unit according to claim 1, wherein the at least one of said conduits extends along a direction substantially parallel with the joint face so that flow within said at least one of said conduits is along a direction substantially parallel with the joint face.

4. The filtration unit according to claim 1, wherein at least one of the members comprises a body topped with at least one of the first flow conduit and the second flow conduit, and said body is arranged substantially symmetrically with respect to the joint face.

5. The filtration unit according to claim 4, wherein the at least one member is formed by moulding a rigid material.

6. The filtration unit according to claim 1, wherein the filtering medium is held in the unit substantially symmetrically with respect to the joint face.

7. The filtration unit according to claim 6, wherein the unit comprises a tight flexible frame wherein the filtering medium is positioned, and said frame is rigidly connected between the sheets along the joint face.

8. The filtration unit according to claim 6, wherein the filtering medium is rigidly connected between the sheets along or at a distance from the joint face.

9. The filtration unit according to claim 1, wherein the outlet compartment is disengaged from the filtering medium by the presence of at least one separating ring arranged between the filtering medium and the flexible outer casing, inside the outlet compartment.

10. The filtration unit according to claim 1, wherein a part of the at least one of the first flow conduit and the second flow conduit extends inside the compartment wherewith said at least one of the first flow conduit and the second flow conduit is connected.

11. The filtration unit according to claim 4, wherein said body comprises a first flat portion and a second rounded portion wherethrough at least one of the first flow conduit passes and the second flow conduit passes.

12. The filtration unit according to claim 4, wherein said body comprises a first part and a second part, each said part having a rounded portion extended on either side by a flat portion, said flat portion being configured to join said two flexible sheets with each of said inlet member and said outlet member respectively.

13. The filtration unit according to claim 12, wherein said body comprises a slot between said first part and said second part, said slot being configured to receive said filtering medium.

14. The filtration unit according to claim 13, wherein said body comprises a conduit passing through said body and opening above said slot, wherein said conduit is configured to connect to a nozzle of a bag system.

15. A bag system for removing target substances from a biological fluid, comprising:
 a filtration unit according to claim 1; and
 a filtrate collection bag, and said filtrate bag being connected to the outlet member of the filtration unit.

* * * * *